US010610682B2

(12) United States Patent
Jolly et al.

(10) Patent No.: US 10,610,682 B2
(45) Date of Patent: Apr. 7, 2020

(54) ELECTRODE LEAD WITH INTEGRATED ATTACHMENT MECHANISM

(71) Applicant: MED-EL Elektromedizinische Geraete GmbH, Innsbruck (AT)

(72) Inventors: Claude Jolly, Innsbruck (AT); Anandhan Dhanasingh, Chennai (IN)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 127 days.

(21) Appl. No.: 15/644,037

(22) Filed: Jul. 7, 2017

(65) Prior Publication Data

US 2017/0304611 A1 Oct. 26, 2017

Related U.S. Application Data

(63) Continuation of application No. 14/561,401, filed on Dec. 5, 2014, now Pat. No. 9,707,388.

(60) Provisional application No. 61/912,180, filed on Dec. 5, 2013.

(51) Int. Cl.
*A61N 1/05* (2006.01)

(52) U.S. Cl.
CPC .......... *A61N 1/0541* (2013.01); *A61N 1/0539* (2013.01); *A61N 1/0558* (2013.01)

(58) Field of Classification Search
CPC ... A61N 1/0539; A61N 1/0541; A61N 1/0558
See application file for complete search history.

(56) References Cited

U.S. PATENT DOCUMENTS

| 4,462,402 | A | 7/1984 | Burgio et al. |
| 5,957,965 | A * | 9/1999 | Moumane ............ A61N 1/0558 607/117 |
| 9,402,990 | B2 * | 8/2016 | Gibson ................ A61N 1/0541 |
| 9,707,388 | B2 | 7/2017 | Jolly et al. |
| 2005/0256561 | A1 | 11/2005 | Gantz et al. |
| 2008/0234793 | A1 | 9/2008 | Gibson |

(Continued)

OTHER PUBLICATIONS

International Searching Authority, International Search Report and Written Opinion, International Application No. PCT/US2014/068719, dated Feb. 10, 2015, 14 pages.

(Continued)

*Primary Examiner* — Amanda K Hulbert
(74) *Attorney, Agent, or Firm* — Sunstein Kann Murphy & Timbers LLP (57) ABSTRACT

An electrode for use with a cochlear implant system includes an electrode array with electrode contacts distributed along the electrode array, and an electrode lead adjacent to the electrode array. The electrode lead has (1) a flexible region configured to allow the electrode lead to bend, (2) an attachment mechanism with an internal portion positioned within and along a longitudinal direction of the electrode lead, and an external portion configured to be bent and secured to bone, the external portion having an attachment element configured to secure the attachment mechanism to the bone, and (3) a securing element extending from the electrode lead and located further back from the flexible region toward a rear end of the electrode lead, the securing element configured to secure the electrode lead to the bone. A method of securing the electrode to bone is also disclosed.

20 Claims, 9 Drawing Sheets

(56) References Cited

U.S. PATENT DOCUMENTS

| | | |
|---|---|---|
| 2008/0312717 A1 | 12/2008 | Gantz |
| 2009/0012592 A1* | 1/2009 | Buysman ................ A61N 1/05 607/116 |
| 2009/0248095 A1 | 10/2009 | Schleicher et al. |
| 2010/0268313 A1 | 10/2010 | Conn |
| 2011/0022101 A1 | 1/2011 | McDonald |

OTHER PUBLICATIONS

Australian Patent Office, Examination Report No. 1 for Application No. 2017204812, dated Jun. 30, 2018, 4 pages.

* cited by examiner

The second component of the mechanism in the form of tube outside the electrode. The mechanism can have extension, that can be cut after electrode insertion or it can be bent to be fixed with bone

ELECTRODE LEAD WITH INTEGRATED ATTACHMENT MECHANISM

CROSS REFERENCE TO RELATED APPLICATIONS

The present application is a continuation of U.S. patent application Ser. No. 14/561,401 filed Dec. 5, 2014, now U.S. Pat. No. 9,707,388, which claims the benefit of U.S. Provisional Patent Application No. 61/912,180 filed Dec. 5, 2013, the disclosures of which are incorporated by reference herein in their entirety.

TECHNICAL FIELD

The present invention generally relates to electrodes for medical implants and, more particularly, the invention relates to electrode leads with integrated attachment mechanisms that secure the electrode to the skull of a patient for use in cochlear implant systems.

BACKGROUND ART

Figure 1:
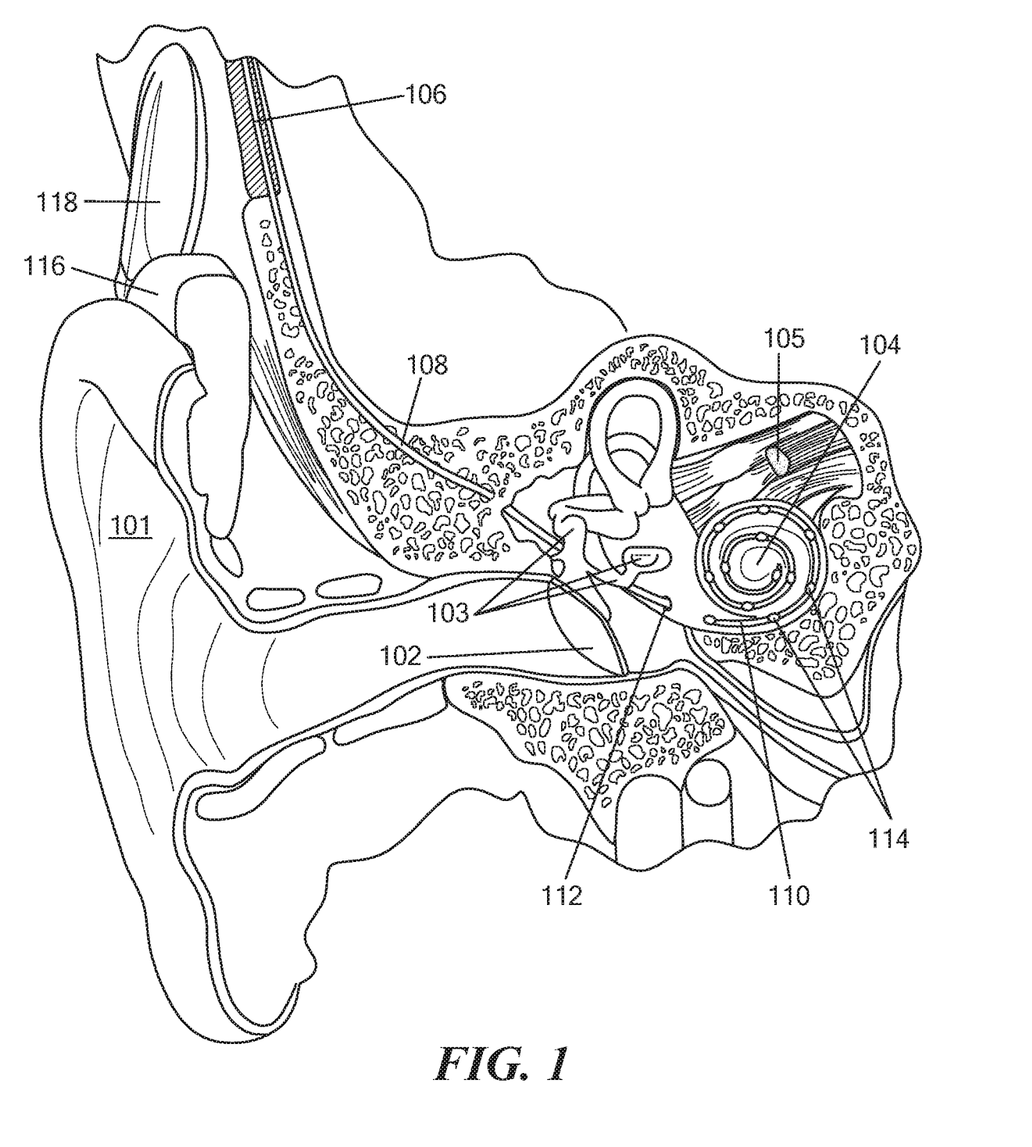
FIG. 1 schematically shows a typical human ear which includes a cochlear implant system.

FIG. 1 schematically shows the anatomy of a normal human ear. The ear typically transmits sounds, such as speech sounds, through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. The cochlea 104 includes three chambers along its length, an upper chamber known as the scala vestibuli, a middle chamber known as the scala media, and a lower chamber known as the scala tympani. The cochlea 104 forms an upright spiraling cone with a center called the modiolus where the axons of the auditory nerve 105 reside. These axons project in one direction to the cochlear nucleus in the brainstem and they project in the other direction to the spiral ganglion cells and neural processes peripheral to the cells in the cochlea. In response to received sounds transmitted by the middle ear 103, sensory hair cells in the cochlea 104 function as transducers to convert mechanical motion and energy into electrical discharges in the auditory nerve 105. These discharges are conveyed to the cochlear nucleus and patterns of induced neural activity in the nucleus are then conveyed to other structures in the brain for further auditory processing and perception.

Hearing is impaired when there are problems in the ability to transmit sound from the external ear to the inner ear, or there are problems in the transducer function within the inner ear. To improve impaired hearing, there are several types of auditory prostheses that have been developed, such as middle ear and inner ear implants, that can restore a sense of partial or full hearing. For example, when the impairment is related to the operation of the middle ear 103, a conventional hearing aid may be used to provide acoustic stimulation to the auditory system in the form of amplified sound. When the impairment is associated with the transducer function in the cochlea 104, a cochlear implant system may be used. Cochlear implant systems can restore some sense of hearing by direct electrical stimulation of the neural tissue of the cochlea. The cochlear implants typically include an implanted electrode 106 having an electrode lead 108 and an electrode array 110. The electrode array 110, which is threaded into the cochlea 104 through an opening in the round window or a cochleostomy site 112, usually includes multiple electrode contacts 114 on its surface that electrically stimulate auditory nerve tissue with small currents delivered by the contacts 114 distributed along the electrode array 110. These electrode contacts 114 are typically located toward the distal end or apical portion of the electrode 106 and are in electrical communication with an electronics module (not shown) that produces an electrical stimulation signal for the implanted electrode contacts 114 to stimulate the cochlea 104. The electrode lead 108 includes the proximal end or basal portion of the implanted electrode 106 that typically goes from the electronics module (e.g., implanted or externally mounted) to the electrode array 110. The electrode lead 108 usually has no electrode contacts, except perhaps a contact that acts as a ground electrode, and encloses the wires that connect to and deliver the electrical stimulation signals to the electrode contacts 114 on the electrode array 110.

In cochlear implant surgery, one surgical technique is a facial recess approach to the middle ear, which involves removing considerable amount of bone in the mastoid region to reach the middle ear region, which is then followed by the opening of the scala tympani either by round window entrance or cochleostomy and the insertion of the electrode array into the cochlea. The facial recess approach is only attempted by experienced surgeons. A recent advancement in this surgical technique involves a minimally invasive procedure in which robot assisted narrow drilling is done in the mastoid bone to reach the middle ear region. The drilling forms a narrow key hole in the mastoid bone, and the electrode is inserted through this key hole. However, there are difficulties with inserting the electrode through this highly porous mastoid bone due to the small size of the hole and also with the subsequent positioning and securing the electrode lead after insertion.

SUMMARY OF EMBODIMENTS

In accordance with one embodiment of the invention, an electrode for use with a cochlear implant system includes an electrode array with at least one electrode contact and an electrode lead adjacent to the electrode array. The electrode lead has a flexible region configured to allow the electrode lead to bend and has an attachment mechanism with an internal portion positioned within the electrode lead and an external portion configured to be bent and secured to bone. In related embodiments, the electrode may be a part of a cochlear implant system.

In accordance with another embodiment of the invention, a method of securing an electrode to bone includes providing the electrode having an electrode array with at least one electrode contact and an electrode lead adjacent to the electrode array. The electrode lead has a flexible region configured to allow the electrode lead to bend and has an attachment mechanism with an internal portion positioned within the electrode lead and an external portion configured to be bent and secured to bone. The method further includes bending the external portion of the attachment mechanism, bending the electrode lead at the flexible region, and securing the external portion of the attachment mechanism and a proximal end of the electrode lead to the bone.

In related embodiments, the flexible region may begin approximately where the external portion of the attachment mechanism extends from within the electrode lead. The flexible region may have a surface profile with a saw-toothed configuration, a sinusoidal configuration, a square wave configuration, and/or a half wave rectified sinusoidal wave configuration. The electrode may further include a securing element disposed on an external surface of the electrode lead. The securing element is configured to hold the external portion of the attachment mechanism to the external surface. The external portion of the attachment mechanism may include two or more wires disposed around the electrode lead. The flexible region may allow a proximal end of the electrode lead to be disposed approximately 90 degrees relative to a distal end of the electrode lead. The electrode may further include a securing element extending from the electrode lead and configured to secure the electrode lead to the bone. The electrode may further include an attachment element configured to secure the external portion of the attachment mechanism to the bone. The external portion of the attachment mechanism may include a sleeve disposed around the electrode lead. The internal portion of the attachment mechanism may extend into a portion of the electrode array. The electrode may further include a basal stiffener configured to surround an external surface of the electrode array and the electrode lead where the electrode lead connects to the electrode array. The external portion of the attachment mechanism and the proximal end of the electrode lead secured to the bone may be disposed approximately 90 degrees relative to a distal end of the electrode lead.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Various embodiments of the present invention provide an electrode lead with an integrated attachment mechanism that is configured to secure the electrode to the skull of a patient for use in cochlear implant systems. The electrode lead includes a flexible region that allows the electrode lead to bend, e.g., 90 degrees or more, so that the rear part of the electrode lead lies flat against the patient's skull after the electrode array is inserted. The electrode lead also includes an attachment mechanism that is partially inside and partially outside of the electrode lead that helps secure the electrode in place. The combination of the flexible region and the integrated attachment mechanism permits the bending and securing of the electrode lead to the bone while preventing the electrode from dislodging from or partially coming out of the narrow insertion hole after electrode insertion. For example, the electrode lead is inserted and secured by the external part of the integrated attachment mechanism to the skull bone and may afterwards be bend. This has the advantage that the electrode lead may not be dislodged due to bending. Details of illustrative embodiments are discussed below.

FIG. 1 shows some components of a typical cochlear implant system that may be used with electrodes according to embodiments of the present invention, although other hearing systems may also be used. The cochlear implant system includes an external microphone (not shown) that provides an audio signal input to an external signal processor 116 where various signal processing schemes may be implemented. The processed signal is then converted into a stimulation pattern by an external transmitter/stimulator 118, and the stimulation pattern/signal is transmitted to an implanted housing (not shown) which transmits the stimulation signal to the implantable electrode 106, such as an electrode 10 according to embodiments of the present invention.

Figure 2A:
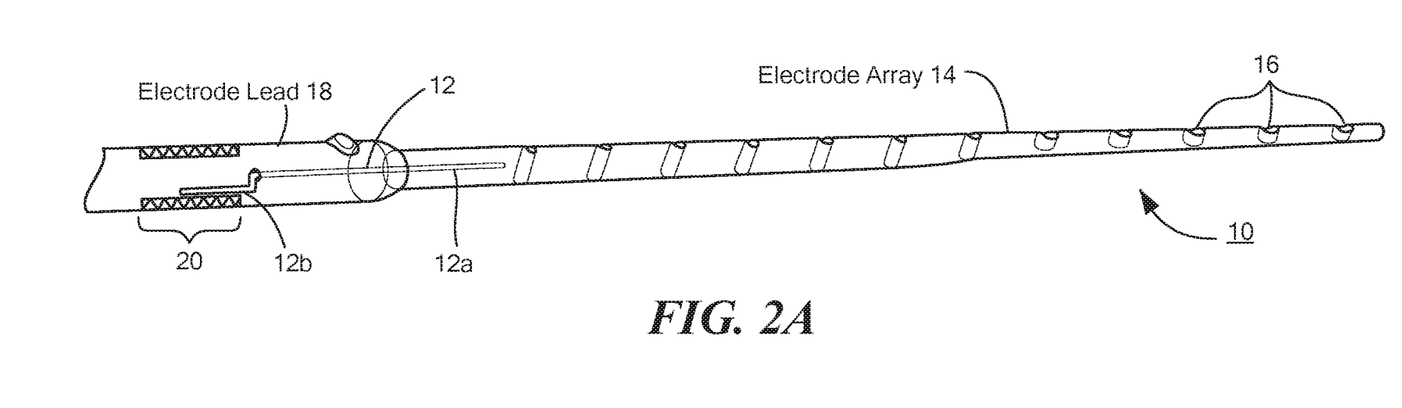
FIGS. 2A and 2B schematically show an electrode with an integrated electrode lead attachment mechanism according to embodiments of the present invention.
Figure 2B:
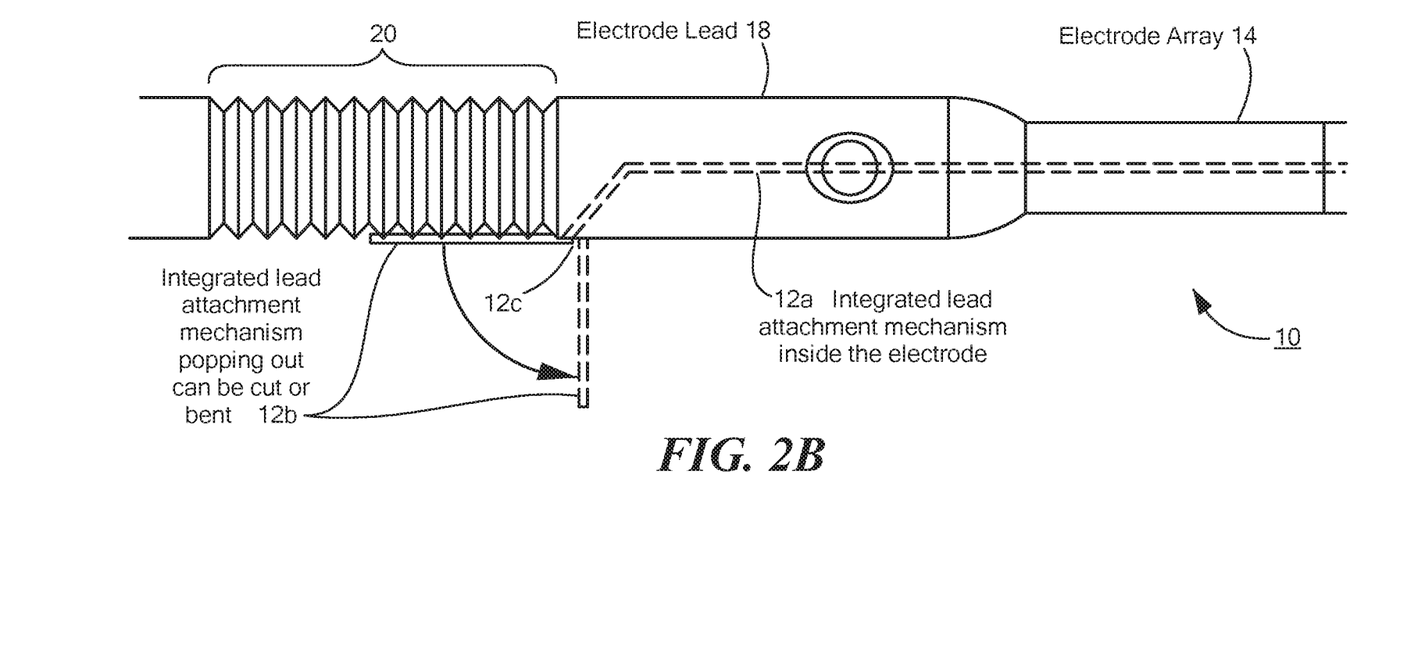

FIGS. 2A and 2B schematically show an electrode 10 with an integrated electrode lead attachment mechanism 12 according to embodiments of the present invention. The electrode 10 includes an electrode array 14, located toward the distal end or apical portion of the electrode 10, having at least one electrode contact 16 and an electrode lead 18, located toward the proximal end or basal portion of the electrode 10, adjacent to the electrode array 14. The electrode lead 18 has an attachment mechanism 12 with an internal portion 12a positioned within the electrode lead 18 (e.g., at a center portion of the electrode) and an external portion 12b that is external to the electrode 10. The internal portion 12a is secured within the electrode lead 18 so that the attachment mechanism 12 is not removable from the electrode lead 18. The attachment mechanism 12 may be formed from any material that can be readily bent and secured to bone. For example, the attachment mechanism 12 may be a medical grade metal rod in which the external portion 12b outside of the electrode lead 18 is formed from a malleable material that can be readily bent or cut and secured to the bone. Alternatively, the external portion 12b of the attachment mechanism 12, or a section of the external portion 12b where the attachment mechanism 12 is to be bent, may have a thinner cross-section or may be thermally treated to have different mechanical properties than the inner portion 12a so that the external portion 12b may be readily bent and secured to the bone.

The electrode lead 18 also has a flexible region 20 configured to allow the electrode lead 18 to bend relative to the part of the electrode lead 18 that includes the internal portion 12a of the attachment mechanism 12. Preferably, the flexible region 20 begins approximately where the internal portion 12a of the electrode lead attachment mechanism 12 transitions to the external portion 12b, shown as 12c in FIG.

Figure 3A:
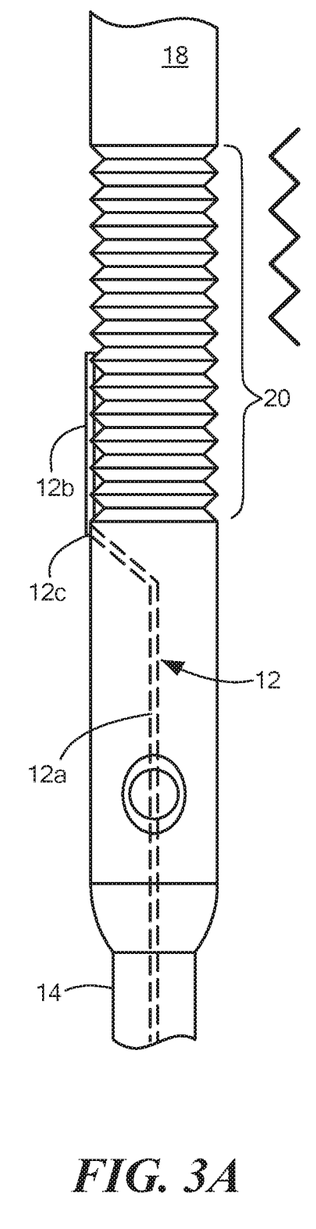
FIGS. 3A-3C schematically show an electrode with various configurations for a flexible region according to embodiments of the present invention.
Figure 3B:
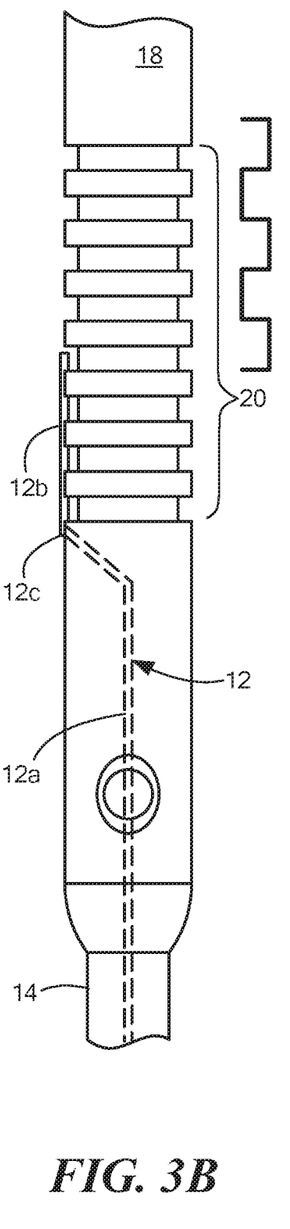
Figure 3C:
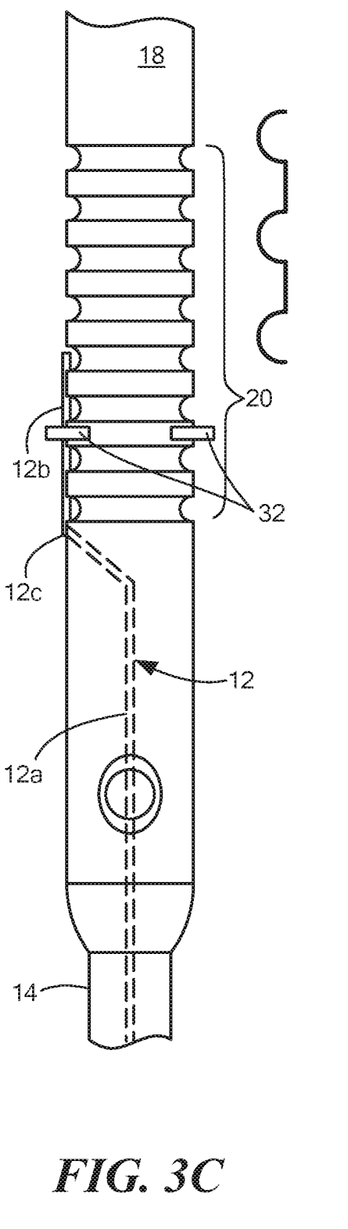

2B, and extends back toward the rear or proximal end 18*a* of the electrode lead 18. The flexible region 20 may be achieved by having a different profile on the surface of the electrode 10 other than a simple cylindrical profile. For example, the surface profile may be a cylinder with a smooth wave configuration (e.g., sinusoidal), a sharp wave configuration (e.g., saw-toothed), a square wave configuration, a truncated sinusoidal configuration (e.g., half wave rectified sinusoidal wave), or any shape that allows for the electrode lead to be readily bent. FIGS. 3A-3C schematically show various configurations for the flexible region 20 of the electrode lead 18, although others may also be used. For example, one side of the electrode 10 may have smaller notches and the other side may have larger notches, so that bending is more easily achieved in one direction compared to the other direction. This has the further advantage that bending along the one direction is predefined and the wires for the electrode contacts within the electrode lead can be positioned properly during manufacturing and thereby improve bending resilience. For example, the wires for the electrode contacts may be arranged in a ribbon band configuration, such that bending along the one predefined direction corresponds to bending along the flat side of the ribbon band.

Figure 4:
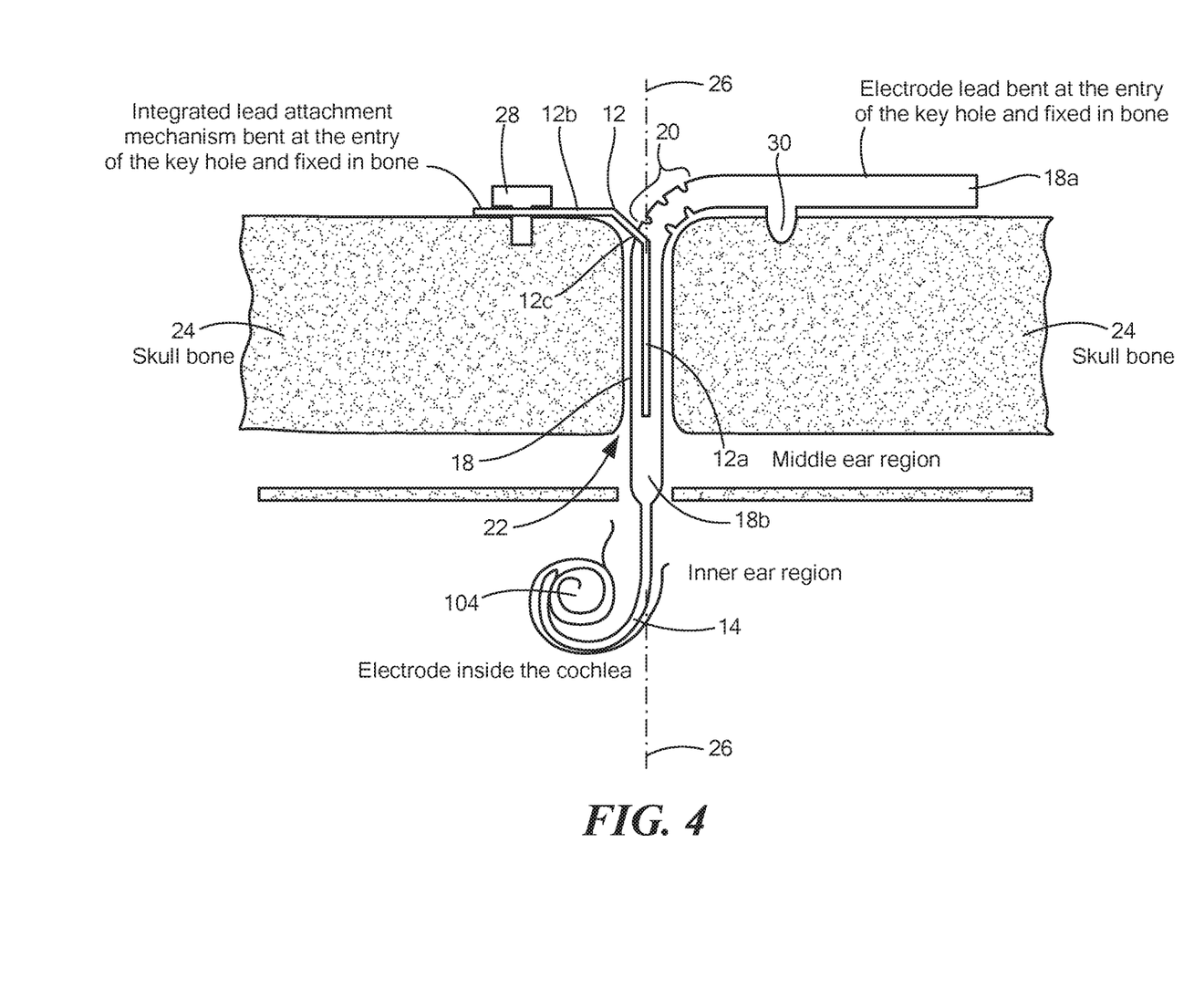
FIG. 4 schematically shows an electrode with an integrated electrode lead attachment mechanism secured to bone according to embodiments of the present invention.

Referring also to FIG. 4, once a narrow hole 22 is formed in the mastoid bone 24, the electrode 10 is inserted through the hole 22 so that the electrode array 14 is placed within the cochlea 104. After the electrode insertion, the rear part or proximal end 18*a* of the electrode lead 18, which is connected to a stimulator, is bent at the flexible region 20 approximately 90° or perpendicular to the axis 26 of the hole 22 or the distal end 18*b* of the electrode lead 18 in order to place the stimulator and the electrode 10 under the skin that covers the skull. To further secure the electrode 10 in place and prevent it from pulling back out of the hole 22 due to this amount of bending, the external portion 12*b* of the attachment mechanism 12 is also bent (e.g., approximately 90° or perpendicular to the axis 26 of the hole 22 or the distal end 18*b* of the electrode lead 18) and secured to the bone 24 by a pin, screw, or other attachment element 28. The proximal end 18*a* of the electrode lead 18 may also have a securing element 30, located further back or toward the rear or proximal end 18*a* of the electrode lead 18 from the flexible region 20, that extends from the external surface of the electrode lead 18. The securing element 30 engages with and secures the electrode lead 18 to the bone 24. As discussed previously, the external portion 12*b* of the attachment mechanism begins approximately where the flexible region 20 begins, so that both the external portion 12*b* and the proximal end 18*a* of the electrode lead 18 may be bent in approximately the same region and secured to the bone 24. Also, it is beneficial to secure the external portion 12*b* of the attachment mechanism 12 to one side of the hole 22 and the proximal end 18*a* of the electrode lead 18 to the other side of the hole 22. For example, the electrode lead 18 may be secured in a recessed channel on the bone 24. To further ensure that the electrode 10 is secured in place, the internal portion 12*a* of the attachment mechanism 12 is preferably at least as long as the thickness of the bone 24 that the hole 22 is formed within, such as shown in FIG. 4.

Figure 5:
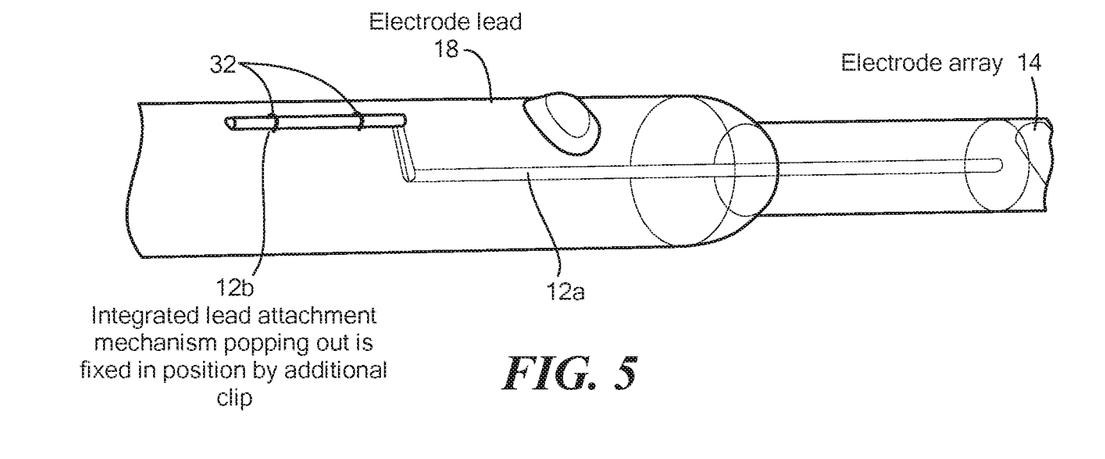
FIG. 5 schematically shows an electrode with additional securing elements holding electrode lead attachment mechanism to electrode lead according to embodiments of the present invention.

During the insertion process, the external portion 12*b* of the attachment mechanism 12 may be releasably secured to the external surface of the electrode lead 18 in order to minimize any trauma to the surrounding area and stabilize the flexible region 20. For example, as shown in FIG. 5, the electrode 10 may include one or more securing elements 32 that fix the external portion 12*b* of the attachment mechanism 12 in place during insertion. The securing element 32 may be located within the flexible region 20 (such as shown in FIG. 3C) or located further back toward the rear or proximal end of the electrode lead 18 beyond the flexible region 20 (not shown). Preferably, the external portion 12*b* of the attachment mechanism 12 extends over the entire length of the flexible region 20 and is releasably fixed to the electrode lead 18 in order to avoid undesired bending of the flexible region 20 during the electrode insertion procedure. Once the insertion process is complete, the external portion 12*b* of the attachment mechanism 12 may be removed from the securing elements 32 in order to bend and secure the external portion 12*b* to the bone 24. Alternatively, or in addition, the external portion 12*b* of the attachment mechanism 12 may be wound around, or otherwise secured in place on, the outside of the electrode lead 18, such as shown in FIG. 6, lending additional support and stiffness to the electrode lead 18 in this area.

Figure 6:
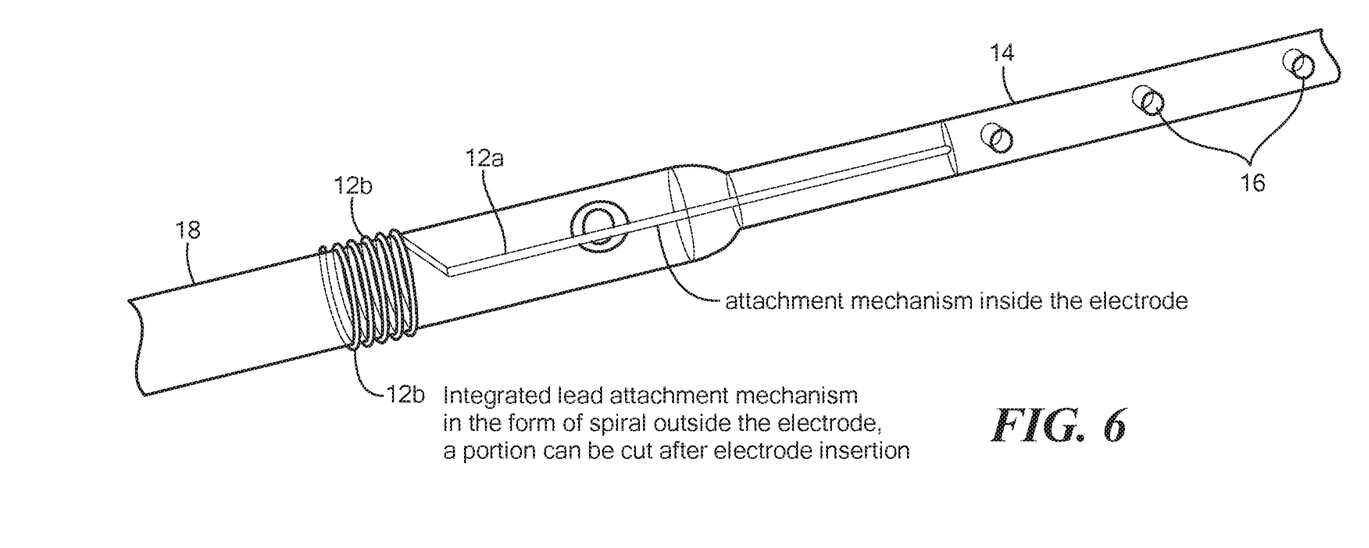
FIG. 6 schematically shows an electrode with electrode lead attachment mechanism secured to electrode lead according to embodiments of the present invention.
Figure 7A:
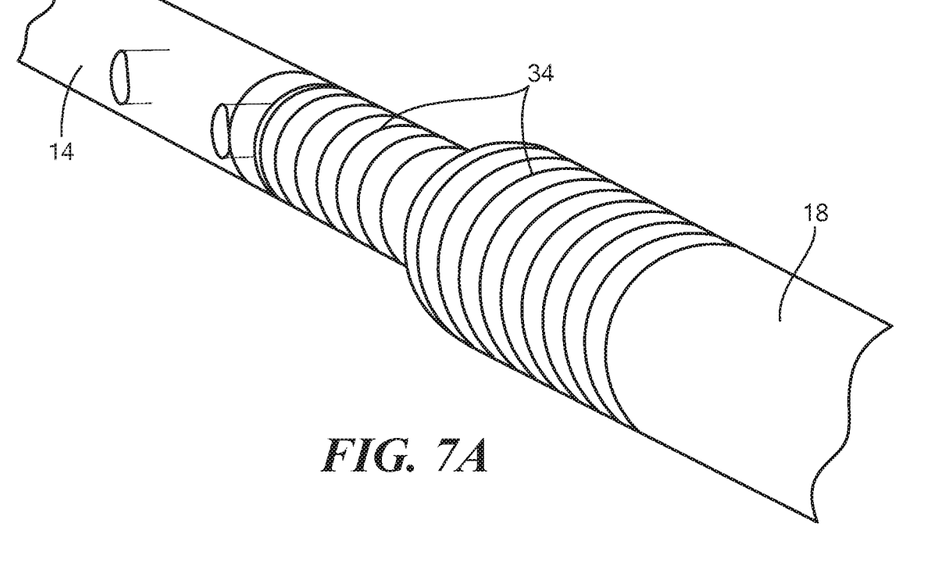
FIGS. 7A and 7B schematically show an electrode with a basal stiffener that may be used with embodiments of the present invention.
Figure 7B:
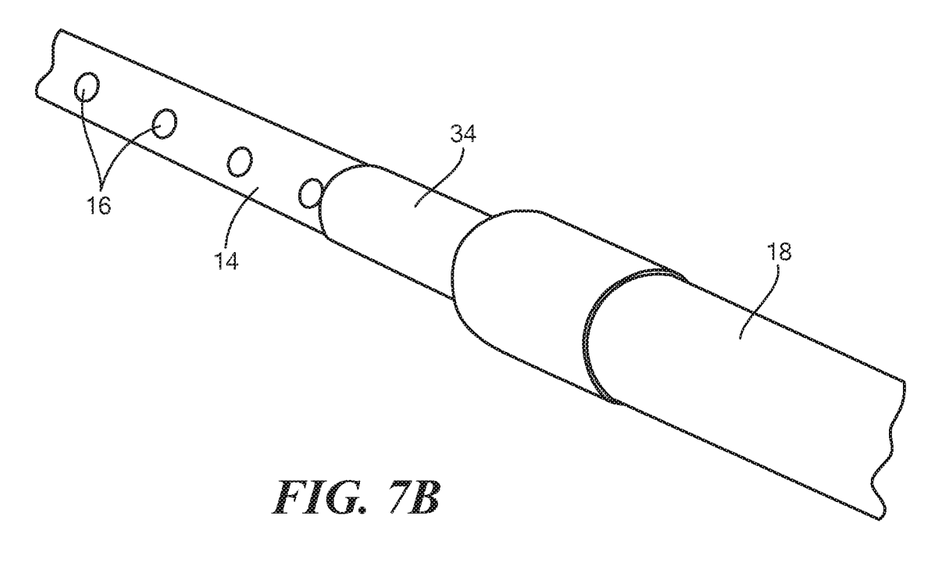

As shown in FIGS. 5 and 6, the internal portion 12*a* of the attachment mechanism 12 may extend into a portion of the electrode array 14 in order to help stabilize the electrode array 14 during the insertion process through the bone 24 and into the cochlea 104. Alternatively, or in addition, the electrode 10 may include a basal stiffener 34, such as shown in FIGS. 7A and 7B, to help during the insertion process. The stiffener 34 may be any biocompatible polymer/metal based material and may be embedded on the outside of the electrode and fixed in place, e.g., using silicone. The stiffener 34 may be in the shape of a spring, such as shown in FIG. 7A, that is wrapped around the external surface of the electrode lead 18 and the electrode array 14, or may be a continuous part or sleeve, such as shown in FIG. 7B. The basal stiffener 34 may be positioned at the junction of the electrode array 14 and the electrode lead 18 where the diameter of the electrode 10 changes in order to help stabilize the electrode array 14.

Figure 8:
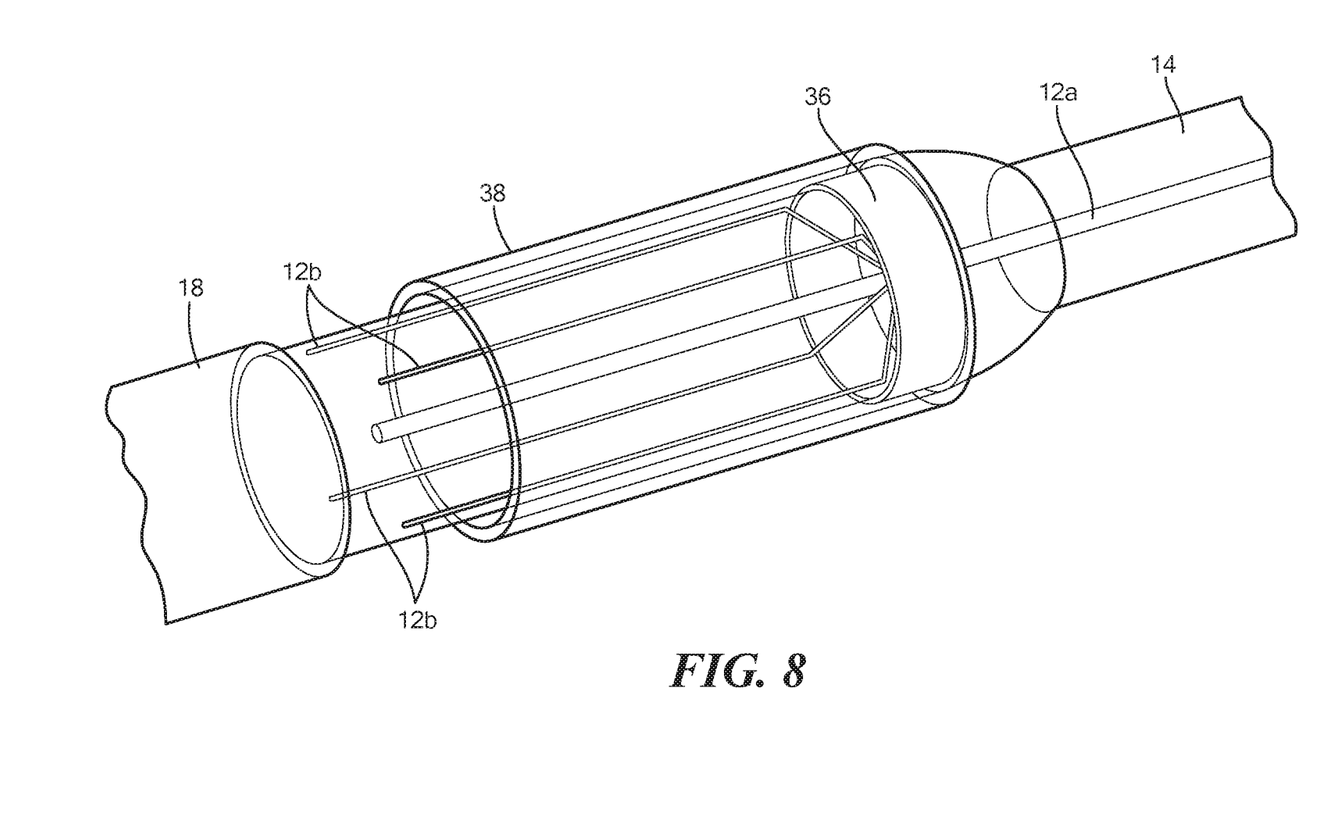
FIG. 8 schematically shows an electrode lead attachment mechanism with an outer ring component according to embodiments of the present invention.

Although the external portion 12*b* of the electrode lead attachment mechanism 12, has been shown as a single rod or wire in the figures above, two or more rods or wires 12*b* may be disposed around the electrode lead 18, such as shown in FIG. 8. In addition, as shown in FIG. 8, the attachment mechanism 12 may further include an external component 36, such as a tube, sleeve, or ring, disposed around and on the outside of the electrode lead 18, attached to the internal portion 12*a*.

Figures 9A, 9B, 9C:
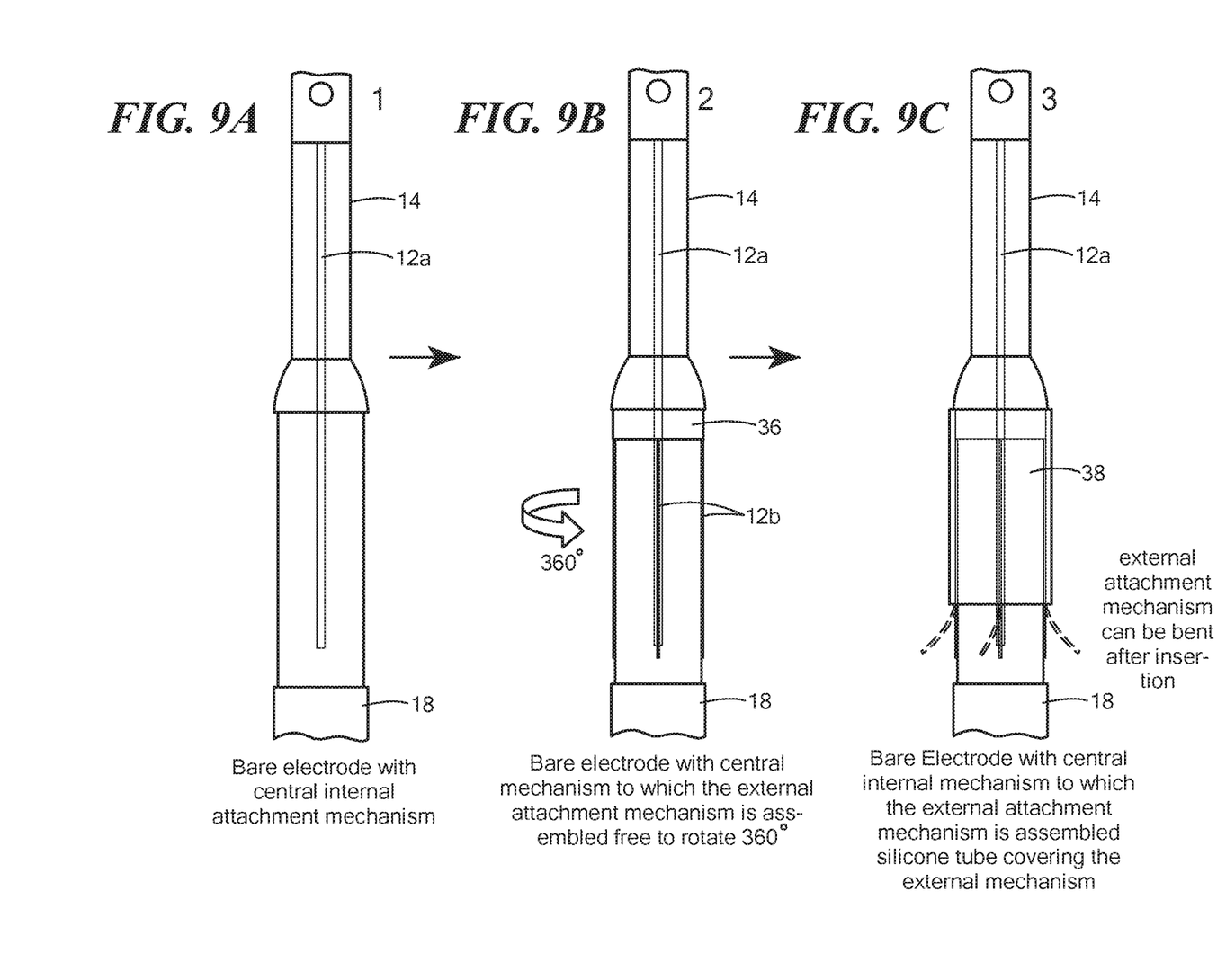
FIGS. 9A-9C schematically show the electrode lead attachment mechanism of FIG. 8 during assembly according to embodiments of the present invention.

Referring also to FIGS. 9A-9C, during assembly, the electrode 10 is formed with the internal portion 12*a* of the attachment mechanism 12, e.g., in the central part of the electrode 10, as shown in FIG. 9A. The external component 36, e.g., in the shape of a ring, is assembled onto the internal portion 12*a*, so that the external component is free to rotate 360 degrees around the electrode lead 18, as shown in FIG. 9B. The external component 36 includes one or more wires or rods 12*b* disposed on the outside of the electrode lead 18 along its longitudinal length. As shown in FIG. 9C, a protective tube 38, e.g., made of silicone, may be placed over the external component 36 and wires 12*b* in order to protect the components during insertion and allow the components to rotate, minimizing the trauma to the surrounding insertion area. As shown in FIG. 9C, the external portion of the attachment mechanism 12*b* may be bent and secured to the bone after the electrode insertion process.

Figure 10:
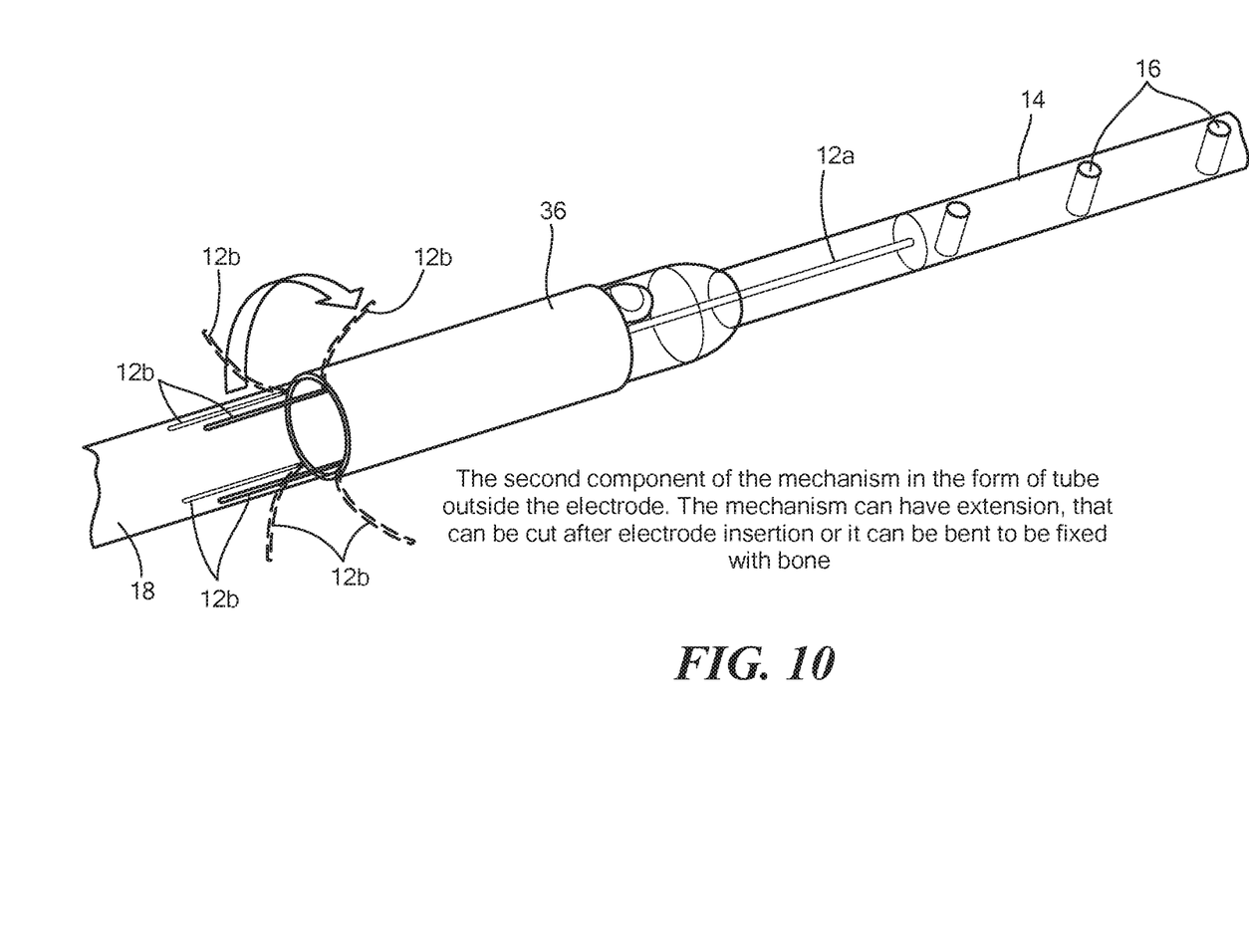
FIG. 10 schematically shows an electrode lead attachment mechanism with an outer sleeve component according to embodiments of the present invention.

FIG. 10 schematically shows another configuration for the external component 36 of the attachment mechanism 12 in the form of a tube disposed around the electrode lead 18. The external portion 12*b* of the attachment mechanism 12 may be attached to and disposed at one end of the external component 36. The one or more wires 12 may be disposed on the outside of the electrode lead 18 along its longitudinal length during the insertion process and then bent or secured to the bone after insertion.

Although the above discussion discloses various exemplary embodiments of the invention, it should be apparent that those skilled in the art can make various modifications that will achieve some of the advantages of these embodiments without departing from the true scope of the invention.

What is claimed is:

1. An electrode for use with a cochlear implant system, the electrode comprising:
    an electrode array with electrode contacts distributed along the electrode array; and
    an electrode lead adjacent to the electrode array, the electrode lead having:
        an integrated attachment mechanism having an internal portion that transitions to an external portion, which is external to the electrode lead, wherein:
            the internal portion is positioned within and along a longitudinal direction of the electrode lead; and
            the external portion is configured to be bent and secured to bone, the external portion having an attachment element configured to secure the attachment mechanism to the bone;
        a flexible region configured to allow a portion of the electrode lead to bend relative to the internal portion of the attachment mechanism, the flexible region located further back toward a proximal end of the electrode lead from where the external portion becomes external to the electrode lead; and
        a securing element extending from the electrode lead and located further back from the flexible region toward the proximal end of the electrode lead such that the flexible region is located between the securing element and where the external portion becomes external to the electrode lead, the securing element configured to secure the electrode lead to the bone.

2. The electrode of claim 1, wherein the flexible region begins approximately where the internal portion of the attachment mechanism transitions to the external portion.

3. The electrode of claim 1, wherein the flexible region has a surface profile with a saw-toothed configuration, a sinusoidal configuration, a square wave configuration, a half wave rectified sinusoidal wave configuration, or combinations thereof.

4. The electrode of claim 1, further comprising a second securing element disposed on an external surface of the electrode lead, the second securing element configured to hold the external portion of the attachment mechanism to the external surface.

5. The electrode of claim 4, wherein the second securing element is located within the flexible region or located further back from the flexible region toward the rear end of the electrode lead.

6. The electrode of claim 1, wherein the external portion of the attachment mechanism includes two or more wires disposed around the electrode lead.

7. The electrode of claim 1, wherein the flexible region allows a proximal end of the electrode lead to be disposed approximately 90 degrees relative to a distal end of the electrode lead.

8. The electrode of claim 1, wherein the external portion of the attachment mechanism includes a sleeve disposed around the electrode lead.

9. The electrode of claim 1, wherein the internal portion of the attachment mechanism extends into a portion of the electrode array.

10. The electrode of claim 1, further comprising a basal stiffener configured to surround an external surface of the electrode array and the electrode lead where the electrode lead connects to the electrode array.

11. A cochlear implant system having an electrode according to claim 1.

12. A method of securing an electrode to bone, the electrode for use with a cochlear implant system, the method comprising:
    providing the electrode according to claim 1,
    bending the external portion of the attachment mechanism,
    bending the electrode lead at the flexible region, and
    securing the attachment element and a proximal end of the electrode lead to the bone.

13. The method of claim 12, wherein the flexible region begins approximately where the internal portion of the attachment mechanism transitions to the external portion.

14. The method of claim 12, wherein the flexible region has a surface profile with a saw-toothed configuration, a sinusoidal configuration, a square wave configuration, a half wave rectified sinusoidal wave configuration, or combinations thereof.

15. The method of claim 12, wherein the electrode further includes a second securing element disposed on an external surface of the electrode lead, the method further comprising holding the external portion of the attachment mechanism to the external surface using the second securing element.

16. The method of claim 15, wherein the second securing element is located within the flexible region or located further back from the flexible region toward the rear end of the electrode lead.

17. The method of claim 12, wherein the external portion of the attachment mechanism includes two or more wires disposed around the electrode lead.

18. The method of claim 12, wherein the secured attachment element and the secured proximal end of the electrode lead are disposed approximately 90 degrees relative to a distal end of the electrode lead.

19. The method of claim 12, wherein the external portion of the attachment mechanism includes a sleeve disposed around the electrode lead.

20. The method of claim 12, wherein the internal portion of the attachment mechanism extends into a portion of the electrode array.

* * * * *